(12) United States Patent
Cho et al.

(10) Patent No.: US 8,168,369 B2
(45) Date of Patent: May 1, 2012

(54) PHOTOACTIVE COMPOUND AND PHOTOSENSITIVE RESIN COMPOSITION CONTAINING THE SAME

(75) Inventors: Chang Ho Cho, Anseong-si (KR); Sung Hyun Kim, Daejeon (KR); Raisa Kharbash, Daejeon (KR); Keon Woo Lee, Daejeon (KR); Dong Kung Oh, Daejeon (KR); Won Jin Chung, Daejeon (KR); Sang Kyu Kwak, Daejeon (KR); Chang Soon Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/147,342

(22) PCT Filed: Feb. 12, 2010

(86) PCT No.: PCT/KR2010/000923
§ 371 (c)(1),
(2), (4) Date: Sep. 19, 2011

(87) PCT Pub. No.: WO2010/093210
PCT Pub. Date: Aug. 19, 2010

(65) Prior Publication Data
US 2011/0318692 A1    Dec. 29, 2011

(30) Foreign Application Priority Data

Feb. 13, 2009 (KR) ................. 10-2009-0011700
Feb. 12, 2010 (KR) ................. 10-2010-0013227

(51) Int. Cl.
*G03F 7/00* (2006.01)
*G03F 7/004* (2006.01)
*G03F 7/028* (2006.01)
*C07D 209/82* (2006.01)

(52) U.S. Cl. ............ 430/270.1; 430/905; 430/281.1; 430/926; 548/440

(58) Field of Classification Search ........ 430/270.1, 430/281.1, 905, 919, 926; 548/440
See application file for complete search history.

(56) References Cited

U.S. PATENT DOCUMENTS

| 7,381,842 | B2 | 6/2008 | Kunimoto et al. |
| 7,648,738 | B2 | 1/2010 | Tanabe et al. |
| 2008/0096115 | A1 | 4/2008 | Tanabe et al. |
| 2010/0075254 | A1 | 3/2010 | Sawamoto et al. |

FOREIGN PATENT DOCUMENTS

| JP | 2006-516246 A | 6/2006 |
| WO | 2008-078686 A1 | 7/2008 |

*Primary Examiner* — Amanda C. Walke
(74) *Attorney, Agent, or Firm* — Rothwell, Figg, Ernst & Manbeck, P.C.

(57) ABSTRACT

The present invention relates to a photoactive compound of a novel structure represented by Chemical Formula 1 below Chemical Formula 1

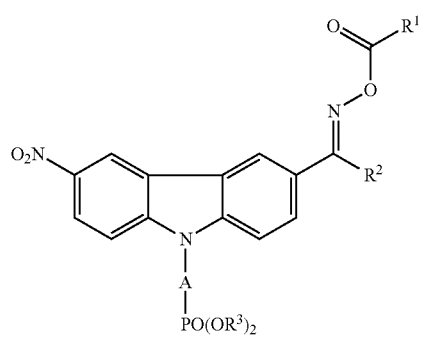

In Chemical Formula 1, $R^1$ and $R^2$, $R^3$, and A are as defined in the specification, and a photosensitive resin composition comprising the same. The photoactive compound of the present invention comprises a nitro group and a phosphonate structure and thus exhibits excellent sensitivity through efficient absorption for UV light, excellent compatibility between the photoactive compound and the alkali-soluble binder resin, and an improved solubility of the photosensitive resin composition. Furthermore, the photosensitive resin composition of the present invention has excellent residual film thickness and mechanical strength characteristics and heat-resistant, chemical-resistant, and development-resistant properties. Accordingly, the photosensitive resin composition of the present invention is advantageous in hardening the column spacers of liquid crystal displays, an overcoat, and passivation materials and also advantageous in a high-temperature process characteristic.

11 Claims, No Drawings

PHOTOACTIVE COMPOUND AND PHOTOSENSITIVE RESIN COMPOSITION CONTAINING THE SAME

CROSS REFERENCE TO RELATED APPLICATIONS

This application is a 35 U.S.C. §371 National Phase Entry Application from PCT/KR2010/000923, filed Feb. 12, 2010, and designating the United States, which claims priority under 35 U.S.C. §119 to Korean patent applications numbers 10-2009-0011700 filed on Feb. 13, 2009 and 10-2010-0013227 filed on Feb. 12, 2010, the entire disclosure of which is incorporated by reference herein, is claimed.

BACKGROUND OF THE INVENTION

1. Field of the Invention

The present invention relates to a photoactive compound having a novel structure and a photosensitive resin composition comprising the same and, more particularly, to a photoactive compound, having high absorptivity for UV light, excellent sensitivity and high-temperature process characteristics, and excellent compatibility in a photosensitive resin composition, and a photosensitive resin composition comprising the photoactive compound.

2. Discussion of the Related Art

A photoactive compound is substance which is decomposed by absorbed light and formed to generate atoms or molecules having activity chemically. The photoactive compound is being widely used in photosensitive resin composition, and so on. Substance having the chemical activity may include, for example, acids, bases, and radicals. In particular, a photoactive compound from which the radicals, from among the acids, bases, and radicals, are generated may be used with acryl groups, generating polymerization along with the radicals, in order to improve the strength of a coated film.

Meanwhile, a photosensitive resin composition may be used to form patterns by coating the photosensitive resin composition on a substrate to form a conductive film, exposing specific portions of the conductive film to light using a photomask, etc., and then developing and removing the non-exposure portions of the conductive film. The photosensitive resin composition is being used in photocurable ink, photosensitive printing sheets, various photoresists, color filter photoresists for LCDs, photoresists for resin black matrices, and transparent photosensitizers because it can be radiated by light, can be polymerized, and hardened.

Furthermore, with the high quality and diversification of LCDs, the photosensitive resin composition is being fabricated to constitute liquid crystal display devices, such as TV and monitors, in addition to display devices for use in the existing notebook computers and mobiles. There is an increasing demand for photosensitive resin compositions, having a fast response to light and mechanically excellent physical properties, in order to improve productivity and durability.

In particular, in the case where patterns are formed by a photolithography method and an insulating protection film is formed through blanket exposure, a characteristic having a fast response to light (that is, photosensitivity) is becoming an important factor. Furthermore, column spacers, playing the role of supports, or an overcoat and a passivation film, playing the role of a protection film, must have excellent mechanical physical properties so that liquid crystal display devices exhibit their original performance without being broken by external shock.

The above problems can be solved by using a photopolymerization initiator with excellent photosensitivity. If the photopolymerization initiator having excellent photosensitivity is used, there are advantages in that a pollution source due to liquid crystals can be reduced, a residual film thickness of patterns can be increased, and other available raw materials when a composition is fabricated can be widely selected because sufficient sensitivity can be implemented even by a small amount of a photopolymerization initiator.

In general, the photopolymerization initiators used in the photosensitive resin composition includes some known kinds, such as acetophenone derivatives, benzophenone derivatives, non-imidazole derivatives, acylphosphine oxide derivatives, triazine derivatives, and oxime ester derivatives. From among them, the oxime ester derivatives are advantageous in that they rarely wear color because they absorb ultraviolet rays, have high radical generation efficiency, and have excellent stability within the composition.

α-oxooxime derivatives, a combined use of thioxanthone and an oxime ester compound, oxime ester in which p-dialkylaminobenzene is used as a synergist, photoinitiators using β-aminooxime, oxime ether photoinitiator comprising ethylene-based unsaturated groups in a molecular structure, and the like have been developed as the photoinitiator of an oxime ester structure. However, the early developed oxime derivative compounds are problematic in that they have low photoinitiation efficiency and they are inefficient in absorbing UV light when they have a good color characteristic.

There have been developments for improving the photoinitiation efficiency, but the developments do not sufficiently achieve a reduction in the turn around time. In particular, the developments are problematic in that they form fine patterns because they do not sufficiently satisfy the degree of cure of a thick film, having a high concentration of pigments and having a coated film of 2.5 μm or higher in thickness. Furthermore, patterns formed by the developments do not satisfy critical dimension (CD) or mechanical strength required for products.

Irgacure OXE 01 or Irgacure OXE 02 (recently commercialized oximeester-based photoinitiators) by CIBA SPECIALTY CHEMICAL CORP. has significantly improved sensitivity, but is disadvantageous in that it may not be used to such a degree that it can exhibit sufficient sensitivity from an economical point of view because it is very expensive and in that the initiator itself has low storage stability.

Accordingly, there is a need for the development of a photoactive compound (that is, a photopolymerization initiator), capable of efficiently absorbing UV light even with a small amount and having excellent sensitivity, high-temperature process characteristic, and solubility, and a photosensitive resin composition comprising the photoactive compound.

SUMMARY OF THE INVENTION

The present invention has been contrived to several problems in conventional photoactive compounds used as photopolymerization initiators which are included in photosensitive resin compositions and problems resulting from the use of the conventional photoactive compounds as photopolymerization initiators of the photosensitive resin composition.

According to the present invention, in a photoactive compound comprising oxime ester as a basic structure, the structure of the photoactive compound is changed so that nitro groups and phosphonate groups are essentially included as substituents. The photoactive compound of the present invention exhibited that it had high absorptivity for UV light and had improved solubility because compatibility with binder resin was excellent, excellent sensitivity, and an excellent process characteristic at high temperature when the photoactive compound was used as a photopolymerization initiator in a photosensitive resin composition.

An object of the present invention is to provide a photoactive compound of a novel structure, comprising oxime ester groups which can efficiently absorb UV light, exhibit excellent sensitivity and an excellent high-temperature process characteristic, and have excellent compatibility in a photosensitive resin composition.

Another object of the present invention is to provide a photosensitive resin composition, comprising the photoactive compound having the above characteristics as a photopolymerization initiator.

DETAILED DESCRIPTION OF THE EMBODIMENTS

A photoactive compound according to the present invention is characterized in that it is represented by Chemical Formula 1 below.

Furthermore, a photosensitive resin composition according to the present invention is characterized in that it comprises the photoactive compound represented by Chemical Formula 1, alkali-soluble binder resin, a polymerizable compound having an ethylene-based unsaturated bond, and a solvent.

Hereinafter, the present invention is described in more detail.

1. Photoactive Compound

The photoactive compound according to the present invention has a structure in accordance with Chemical Formula 1.

Chemical Formula 1

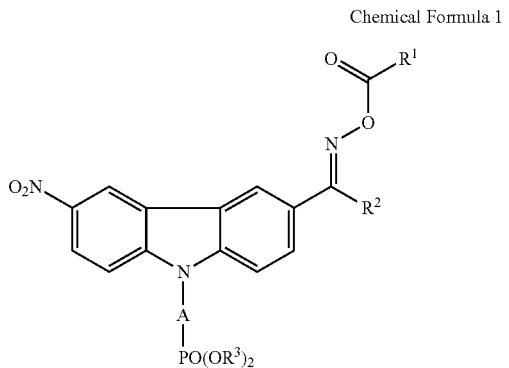

In Chemical Formula 1, each of $R^1$ and $R^2$ independently is hydrogen, halogen, cyano, —R, —OR, —SR, —COR, —OCOR, NRR', or —CONRR' group, $R^3$ is an alkyl group of C1 to C8 or an aryl group of C6 to C12, A is an alkylene group of C2 to C15 which is unsubstituted or substituted with one or more substituents selected from the group consisting of —R, —OR, —SR, —COR, and —OCOR groups, Here, each of the R and R' is an alkyl group of C1 to C10, a halo alkyl group of C1 to C10, or an aralkyl group of C7 to C13, or R and R' together can form a ring.

In Chemical Formula 1, $R^1$ is a portion decomposed into radicals (that is, active species) upon exposure and is not limited to a special structure, but is preferably a methyl group or a phenyl group. The methyl group or the phenyl group can improve photoinitiation efficiency because it has a simple structure and good movement.

In Chemical Formula 1, it is more preferred that $R^2$ be a methyl group or a diheptyl group in terms of solubility and compatibility.

In Chemical Formula 1, it is preferred that $R^3$ be a methyl group or an ethyl group.

In Chemical Formula 1, it is more preferred that A be a hexylene group or a propylene group in terms of solubility and compatibility.

The photoactive compound of the present invention, represented by Chemical Formula 1, is characterized in that it basically comprises an oxime ester group within its structure and comprises a nitro group (—$NO_2$) and a phosphonate group (C—PO(OR$^3$)$_2$.

The nitro group functions to move a maximum UV absorption wavelength of the compound, represented by Chemical Formula 1, about 370 nm (that is, a long wavelength) so that light of an i-line ($\lambda$=365 nm) (that is, a maximum emission wavelength of a common mercury light exposure device can be efficiently absorbed, thereby improving sensitivity.

Furthermore, the phosphonate group functions to increase the solubility of the compound represented by Chemical Formula 1, to improve the solubility of a photosensitive resin composition by means of high compatibility with binder resin by forming hydrogen bonds with alkali-soluble binder resin in the photosensitive resin composition, and to lower volatility. According to the above structural characteristic, the photoactive compound of the present invention has a high sensitivity characteristic, an excellent solubility characteristic, and a low volatility characteristic, as compared with conventional photoactive compounds including oxime ester. If the photoactive compound of the present invention is used in a photosensitive resin composition as a photopolymerization initiator, a sensitivity characteristic, chemical-resistant properties, development-resistant properties, the degree of cure, and a high-temperature process characteristic can be improved.

Meanwhile, a method of manufacturing the photoactive compound represented by Chemical Formula 1 according to the present invention is not specially limited, but may be fabricated using the following method.

First, haloalkylcarbazole is obtained by reacting carbazole with haloalkane, such as dibromo alkane or bromochloro alkane. A phosphonate compound is obtained by reacting the haloalkylcarbazole with trialkylphosphite. A nitrocarbazole compound is obtained by reacting the phosphonate compound with copper nitrate. An acyl compound is obtained by reacting the nitrocarbazole compound with acid chloride in the presence of aluminum chloride. An oxime compound is obtained by reacting the acyl compound with cyclolamine hydrochloride. An oxime ester photoactive compound represented by Chemical Formula according to the present invention is obtained by reacting the oxime ester photoactive compound with acid anhydrides or acid chlorides.

The reaction formula is shown in detail in Reaction Formula 1 below.

Reaction Formula 1

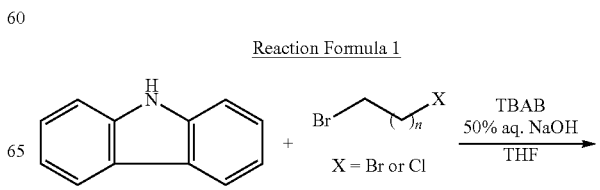

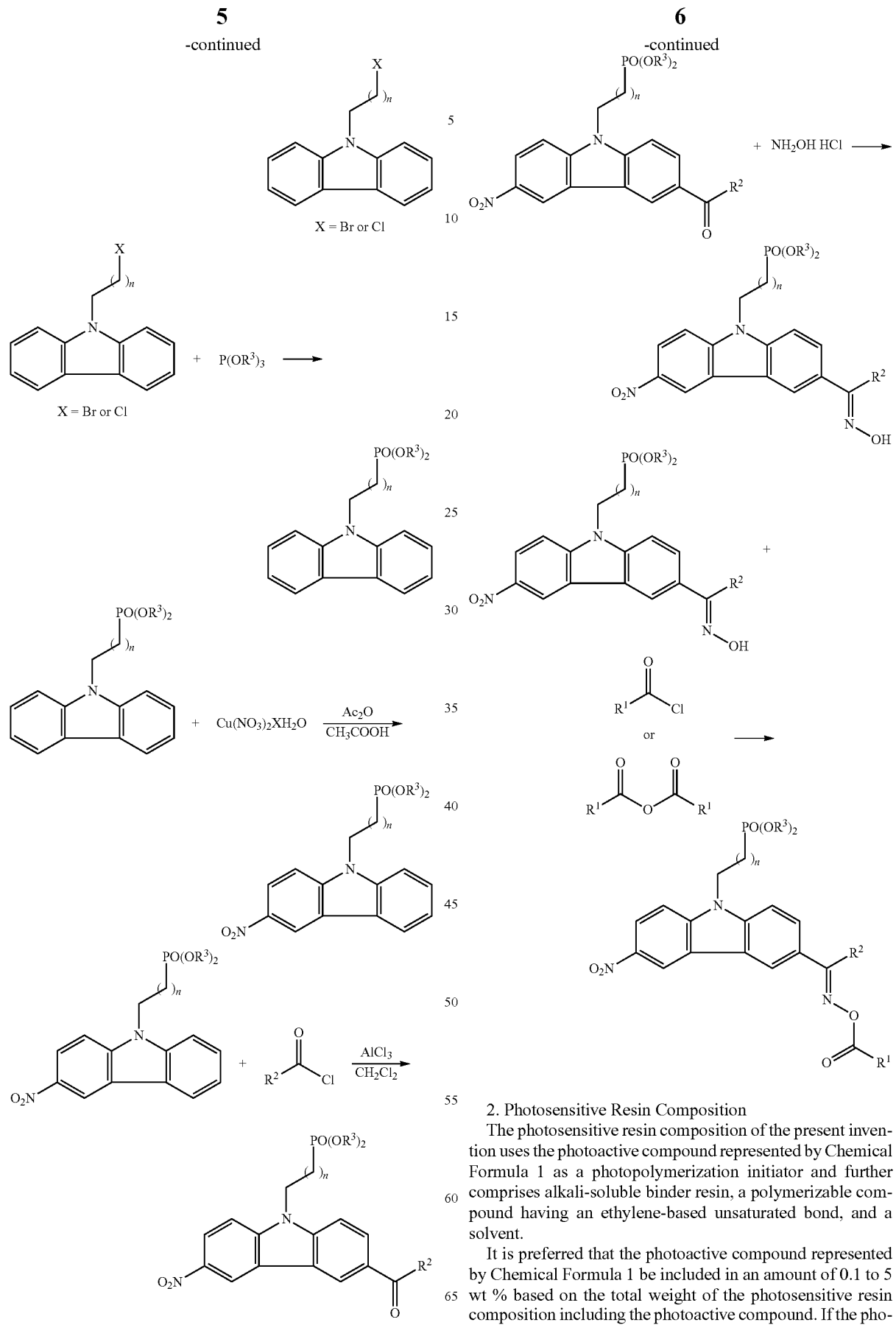

2. Photosensitive Resin Composition

The photosensitive resin composition of the present invention uses the photoactive compound represented by Chemical Formula 1 as a photopolymerization initiator and further comprises alkali-soluble binder resin, a polymerizable compound having an ethylene-based unsaturated bond, and a solvent.

It is preferred that the photoactive compound represented by Chemical Formula 1 be included in an amount of 0.1 to 5 wt % based on the total weight of the photosensitive resin composition including the photoactive compound. If the photoactive compound represented by Chemical Formula 1 is included in an amount of less than 0.1 wt %, sufficient sensitivity may not be exhibited. If the photoactive compound represented by Chemical Formula 1 is included in an amount of more than 5 wt %, UV light may not be transferred to the bottom because of high UV absorption.

In the photosensitive composition according to the present invention, the alkali-soluble resin binder may be a compound which is fabricated using a monomer comprising an acid functional group, a copolymer with a monomer copolymerizable with the monomer comprising the acid functional group, or an ethylene-based unsaturated compound, comprising the copolymer and an epoxy group, through a polymer reaction.

Unlimited examples of the monomer comprising the acid functional group may comprise (meth)acrylic acid, crotonate, itaconic acid, maleic acid, fumarates, monomethyl maleic acid, isoprene sulfonic acid, styrene sulfonic acid, 5-norbornene-2-carboxylic acid, mono-2-((meth)acryloyloxy)ethyl phthalates, mono-2-((meth)acryloyloxy)ethyl succinates, ω-carboxy polycaprolactone mono(meth)acrylates, and one selected from the group consisting of a mixture of them.

Unlimited examples of the copolymer with the monomer copolymerizable with the monomer comprising the acid functional group may comprise unsaturated carboxylic acid esters selected from the group consisting of benzyl(meth)acrylate, methyl(meth)acrylate, ethyl(meth)acrylate, butyl(meth)acrylate, dimethylaminoethyl(meth)acrylate, isobutyl(meth)acrylate, t-butyl(meth)acrylate, cyclohexyl(meth)acrylate, isorbonyl(meth)acrylate, ethylhexyl(meth)acrylate, 2-phenoxyethyl(meth)acrylate, tetrahydrofurfuryl(meth)acrylate, hydroxyethyl(meth)acrylate, 2-hydroxypropyl(meth)acrylate, 2-hydroxy-3-chloropropyl(meth)acrylate, 4-hydroxybutyl(meth)acrylate, acyloctyloxy-2-hydroxypropyl(meth)acrylate, glycerol(meth)acrylate, 2-methoxyethyl(meth)acrylate, 3-methoxybutyl(meth)acrylate, ethoxydiethyleneglycol(meth)acrylate, methoxytriethyleneglycol(meth)acrylate, methoxytripropyleneglylcol(meth)acrylate, poly(ethylene glycol)methylether(meth)acrylate, phenoxydiethyleneglycol(meth)acrylate, p-nonylphenoxypolyethyleneglycol(meth)acrylate, p-nonylphenoxypolypropyleneglylcol(meth)acrylate, tetrafluoropropyl(meth)acrylate, 1,1,1,3,3,3-hexafluoroisopropyl(meth)acrylate, octafluoropentyl(meth)acrylate, heptadecafluorodecyl(meth)acrylate, tribromophenyl(meth)acrylate, methyl α-hydroxymethyl acrylate, ethyl α-hydroxymethyl acrylate, propyl α-hydroxymethyl acrylate, butyl α-hydroxymethyl acrylate, dicyclofentanyl(meth)acrylate, dicyclopentenyl(meth)acrylate, dicyclofentanyl oxyethyl(meth)acrylate, and dicyclopentenyl oxyethyl(meth)acrylate;

aromatic vinyl kinds selected from the group consisting of styrene, α-methylstyrene, (o,m,p)-vinyl toluene, (o,m,p)-methoxy styrene, and (o,m,p)-chloro styrene;

unsaturated ethers selected from the group consisting of vinyl methyl ether, vinyl ethyl ether, and allyl glycidyl ether;

N-vinyl tertiary amines selected from the group consisting of N-vinyl pyrrolidone, N-vinyl carbazole, and N-vinyl morpholine;

unsaturated imides selected from the group consisting of N-phenyl maleimide, N-(4-chlorophenyl)maleimide, N-(4-hydroxyphenyl)maleimide, and N-cyclohexyl maleimide;

anhydride maleic acid, such as anhydride maleic acid or anhydride methyl maleic acid;

unsaturated glycidyl compound kinds selected from the group consisting of allyl glycidyl ether, glycidyl(meth)acrylate, and 3,4-epoxycyclohexylmethyl(meth)acrylate; and a mixture of them.

The alkali-soluble binder resin used in the present invention has an acid value of about 30 to 300 KOH mg/g. If the acid value of the alkali-soluble binder resin is less than 30 KOH mg/g, clean patterns cannot be obtained because the alkali-soluble binder resin is not properly developed. Furthermore, if the acid value exceeds 300 KOH mg/g, patterns may be fallen off because a washing characteristic is excessively improved.

Furthermore, the weight average molecular weight of the alkali-soluble binder resin preferably is in the range of 1,000 to 200,000, more preferably, in the range of 5,000 to 100,000. If the weight average molecular weight of the alkali-soluble binder resin is less than 1,000, heat-resisting and chemical-resistant properties are deteriorated. Furthermore, if the weight average molecular weight of the alkali-soluble binder resin exceeds 200,000, the alkali-soluble binder resin is rarely developed because solubility for a developer is low and uniform coating is difficult because the viscosity of a solution is excessively increased.

It is preferred that the alkali-soluble binder resin be included in an amount of 1-20 wt % based on the total weight of the photosensitive resin composition including the alkali-soluble binder resin. If the contents of the alkali-soluble binder resin are less than 1 wt %, patterns are difficult to form because solubility for a developer is not generated. If the contents of the alkali-soluble binder resin exceed 20 wt %, there is a difficulty in coating because the viscosity of the total solution is excessively increased.

The polymerizable compound having the ethylene-based unsaturated bond may comprise one or more kinds selected from the group consisting of:

a compound obtained by esterifying polyhydric alcohol of a mixture of dipentaerythritol hexa(meth)acrylate and of an acid variant of ethyleneglycol di(meth)acrylate, polyethylene glycol di(meth)acrylate in which the number of ethylene groups is 2 to 14, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic, propylene glycol di(meth)acrylate in which the number of propylene groups is 2 to 14, dipentaerythritol pentameth)acrylate, dipentaerythritol pentameth)acrylate, or dipentaerythritol hexa(meth)acrylate using α,β-unsaturated carboxylic acid;

a compound obtained by adding (meth)acrylic acid to a compound containing a glycidyl group, such as a trimethylolpropane triglycidyletheracrylic acid adduct or a bisphenol A diglycidyletheracrylic acid adduct;

an adduct of a compound having an OH group or an ethylene-based unsaturated bond, such as phthlatediester of β-hydroxyethyl(meth)acrylate, and a toluene diisocyanate adduct of β-hydroxyethyl(meth)acrylate, and an ester compound with polyhydric carboxylic acid, or polyisocyanate, wherein the compound having the ethylene-based unsaturated bond is one or more kinds selected from the group consisting of allyl glycidyl ether, glycidyl(meth)acrylate, 3,4-epoxycyclohexylmethyl(meth)acrylate, glycidyl 5-norbornene-2-methyl-2-carboxylate(endo, exo mixture), 1,2-epoxy-5-hexene, and 1,2-epoxy-9-decene;

(meth)acrylic acid alkylester selected from the group consisting of methyl(meth)acrylate, ethyl(meth)acrylate, butyl(meth)acrylate, and 2-ethylhexyl(meth)acrylate; and 9,9'-bis[4-(2-acryloyloxyethoxy)phenyl]fluorene, but not limited thereto. Polymerization compounds known in the art to which the present invention pertains may be used.

Furthermore, silica dispersion may be used in the compounds as occasion demands. For example, Nanocryl XP series (0596, 1045, 21/1364) or Nanopox XP series (0516, 0525) (fabricated by HANSE CHEMIE AG) may be used in the above compounds.

It is preferred that the polymerizable compound having the ethylene-based unsaturated bond be included in an amount of 0.5-20 wt % based on the total weight of the photosensitive resin composition including the polymerizable compound. If the contents of the ethylene-based unsaturated compound are less than 0.5 wt % less, it is not preferred because a crosslinking reaction by light is not performed. If the contents of the ethylene-based unsaturated compound exceed 20 wt %, there is a disadvantage in that patterns are difficult to form because solubility for alkali is low.

In the photosensitive resin composition according to the present invention, unlimited examples of the solvent may comprise one or more kinds selected from the group consisting of methyl ethyl ketone, methylcellosolve, ethylcellosolve, ethyleneglycol dimethyl ether, ethyleneglycol diethyl ether, propyleneglylcol dimethyl ether, propyleneglylcol diethyl ether, diethyleneglycol dimethylether, diethyleneglycol diethylether, diethyleneglycol methyl ethyl ether, 2-ethoxy propanol, 2-methoxy propanol, 3-methoxy butanol, cyclohexanone, cyclopentanone, propyleneglylcol methyl ether acetate, propyleneglylcol ethyl ether acetate, 3-methoxybutyl acetate, ethyl 3-ethoxypropionate, ethyl cellosolveacetate, methyl cellosolveacetate, butyl acetate, and dipropyleneglylcol monomethyl ether.

It is preferred that the photosensitive resin composition of the present invention comprise the photoactive compound (0.1 to 5 wt %) represented by Chemical Formula 1, the polymerizable compound (0.5 to 20 wt %) having the ethylene-based unsaturated bond, the alkali-soluble binder resin of 1 to 20 wt %, and the solvent of 10 to 95 wt %.

The photosensitive composition according to the present invention may further comprise one or more kinds of additives, such as a second photoactive compound, a hardening accelerator, a thermal polymerization inhibitor, a plasticizer, an adhesive accelerator, a filler, and a surfactant, in addition to the above components.

Unlimited examples of the second photoactive compound may comprise one or more kinds selected from the group consisting of:

a triazine-based compound selected from the group consisting of 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-{4-[2,4-bis(trichloromethyl)-s-triazine-6-1]phenylthio}propanoic acid, 2,4-trichloromethyl-(4'-ethylbiphenyl)-6-triazine, and 2,4-trichloromethyl-(4'-methylbiphenyl)-6-triazine;

a non-imidazole compound selected from the group consisting of 2,2'-bis(2-chlorophenyl)-4,4',5,5'-tetraphenyl non-imidazole and 2,2'-bis(2,3-dichlorophenyl)-4,4',5,5'-tetraphenylnon-imidazole;

an acetophenon-based compound selected from the group consisting of 2-hydroxy-2-methyl-1-phenylpropane-1-one, 1-(4-isopropylphenyl)-2-hydroxy-2-methylpropane-1-one, 4-(2-hydroxyethoxy)-phenyl(2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propane-1-one (Irgacure-907), and 2-benzyl-2-dimethylamino-1-(4-morpholinophenyl)-butane-1-one (Irgacure-369);

an O-acyloxime-based compound, such as Irgacure OXE 01 or Irgacure OXE 02 (fabricated by CIBA GEIGY AG);

a benzophenone-based compound, such as 4,4'-bis(dimethylamino)benzophenone or 4,4'-bis(diethylamino)benzophenone;

a tioxanthene-based compound selected from the group consisting of 2,4-diethyl tioxanthene, 2-chloro tioxanthene, isopropyl tioxanthene, and diisopropyl tioxanthene;

a phosphine oxide-based compound selected from the group consisting of 2,4,6-trimethylbenzoyl diphenylphosphine oxide, bis(2,6-dimethoxybenzoyl)-2,4,4-trimethylpentyl phosphine oxide, and bis(2,6-dichlorobenzoyl)propyl phosphine oxide; and a courmarin-based compound selected from the group consisting of 3,3'-carbonylvinyl-7-(diethylamino)courmarin, 3-(2-benzothiazolyl)-7-(diethylamino)courmarin, 3-benzoyl-7-(diethylamino)courmarin, 3-benzoyl-7-methoxycourmarin, and 10,10'-carbonylbis[1,1,7,7-tetramethyl-2,3,6,7-tetrahydro-1H,5H,11H—Cl]-benzopyrano[6,7,8-ij]-quinolizin-11-one.

The hardening accelerator may include, for example, one or more kinds selected from the group consisting of 2-mercaptobenzoimidazol, 2-mercaptobenzothiazolyl, 2-mercaptobenzooxazol, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate), but not limited thereto. Hardening accelerators known in the art to which the present invention may be used.

The thermal polymerization inhibitor may include one or more kinds selected from the group consisting of p-anisole, hydroquinone, pyrocatechol, t-butyl catechol, N-nitrosophenylhydroxyamine ammonium salts, N-nitrosophenylhydroxyamine aluminum salts, and phenothiazine, but not limited thereto. Thermal polymerization inhibitors known in the art to which the present invention may be used.

All compounds that may be included in conventional photosensitive resin compositions may be used as the plasticizer, the adhesive accelerator, the filler, and the surfactant used in the present invention.

If different components are added to the photosensitive resin composition of the present invention, it is preferred that the second photoactive compound be included in an amount of 0.1 to 5 wt % and each of other additives be included in an amount of 0.01 to 5 wt % based on the total weight of the photosensitive resin composition including the second photoactive compound and other additives.

The photosensitive resin composition according to the present invention is used in a roll coater, a curtain coater, a spin coater, a slot die coater, and various printings and depositions and may be applied on supports, such as a metallic, paper, or glass plastic substrate.

Furthermore, after the photosensitive resin composition is coated on a support, such as a film, the photosensitive resin composition may be transferred to other supports or may be coated on a first support, transferred to a blanket, etc., and then transferred to a second support. A method of using the photosensitive resin composition is not specially limited.

A light source for hardening the photosensitive resin composition of the present invention may include, for example, mercury vapor arc, carbon arc, or Xe arc which emits light having a wavelength of 250 to 450 nm.

The photosensitive resin composition according to the present invention may be used to fabricate photocurable pigments, photocurable ink, pigment-dispersed photosensitizers for fabricating TFT LCD color filters, and photosensitizers for forming the black matrices of TFT LCDs or organic light-emitting diodes, but not limited thereto.

Hereinafter, some exemplary embodiments of the present invention are suggested in order to help understanding of the present invention. However, the following embodiments are provided only to more easily understand the present invention, and it is to be understood that the present invention is not limited to the embodiments. Furthermore, the following embodiments show only some examples of the present invention, and it will be evident to a person having ordinary skill in the art that equivalents of the embodiments may have the same effects as the present invention.

Embodiment 1: Manufacture of a Photoactive Compound 1

(1) Manufacture of 9-(6-bromohexyl)-carbazole(9-(6-bromohexyl)-carbazole) 1b

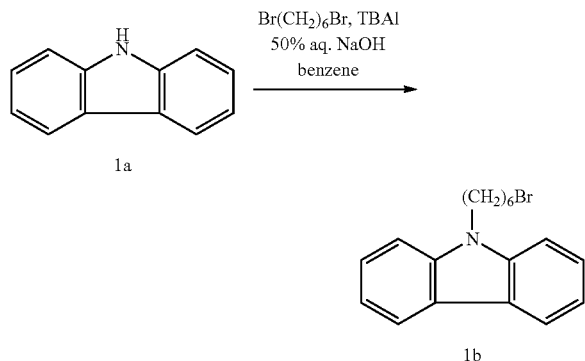

Tetrabutylammoniumiodide (0.5 g, 1.7 mmol), 1,6-dibromohexane (18.2 g, 74.7 mmol), and a 50% aqueous sodium hydroxide solution of 40 mL were slowly added to a solution in which carbazole (10.0 g, 59.8 mmol) represented by the above 1a was dissolved in benzene of 40 mL, under a nitrogen atmospheric current. The mixture was stirred in a temperature of 80° C. for 3 hours. Next, an organic layer was separated from the solution by adding ethylacetate of 50 g and water of 50 g to the solution. Next, water was removed from the solution by using anhydride sodiumsulfate, and solvents were removed under vacuum. 9-(6-bromohexyl)-carbazole of 15.5 g represented by the above 1b was obtained by washing the solution using hexane and by drying it under vacuum (Yield: 78%). A measurement result using $^1$H-NMR of the 9-(6-bromohexyl)-carbazole is listed below.

1H NMR (500 MHz, CDCl$_3$, ppm): 8.10 (2H, d, ArH), 7.46 (2H, t, ArH), 7.39 (2H, d, ArH), 7.23 (2H, t, ArH), 4.32 (2H, t, CH$_2$), 3.36 (2H, t, CH$_2$), 1.97-1.91 (2H, m, CH$_2$), 1.85-1.79 (2H, m, CH$_2$), 1.54-1.48 (2H, m, CH$_2$), 1.44-1.39 (2H, m, CH$_2$).

(2) Manufacture of 1c

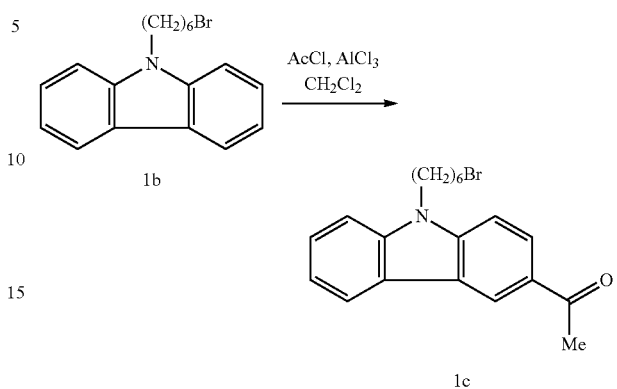

The compound 1b (6.0 g, 18.3 mmol) obtained by the manufacture (1) and acetylchloride (1.4 g, 18.3 mmol) were dissolved in dichloromethane of 50 mL, and aluminum chloride (2.6 g, 18.3 mmol) was then divided and slowly added in a temperature range of 0 to 10° C. The solution was further stirred in the temperature range of 0 to 10° C. for 2 hours and then was further stirred at normal temperature for 12 hours. After the reactant was poured into a beaker containing iced water, an organic layer was extracted from the reactant. After the reactant was washed using a saturated NaHCO$_3$ aqueous solution, water was removed from the reactant using anhydride sodiumsulfate. Acylating 1c of 2.3 g was obtained by removing solvents from the solution under vacuum and then refining the solution using column (hexane/ethylacetate=4/1) (Yield: 34%). Measurement results using $^1$H-NMR of the acylating 1c are as follows.

1H NMR (500 MHz, CDCl$_3$, ppm): 8.74 (1H, s, ArH), 8.16-8.15 (1H, d, ArH), 8.13-8.11 (1H, d, ArH), 7.53-7.50 (1H, t, ArH), 7.43-7.42 (1H, d, ArH), 7.40-7.38 (1H, d, ArH), 7.32-7.29 (1H, t, ArH), 4.34-4.31 (2H, t, CH$_2$), 3.37-3.35 (2H, t, CH$_2$), 2.72 (3H, s, COCH$_3$), 1.93-1.87 (2H, m, CH$_2$), 1.83-1.78 (2H, m, CH$_2$), 1.51-1.45 (2H, m, CH$_2$), 1.42-1.37 (2H, m, CH$_2$).

(3) Manufacture of 1d

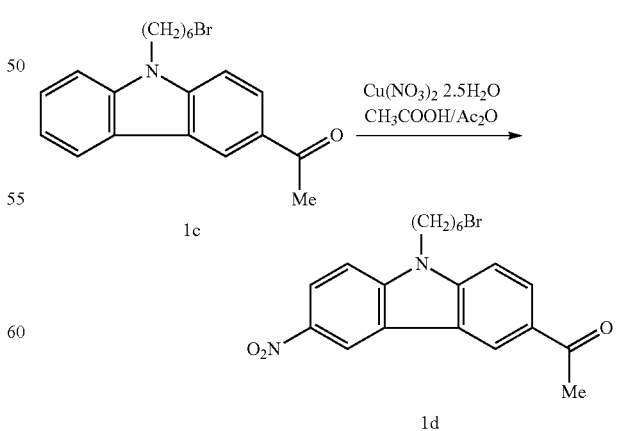

After copper nitrate hydrate (1.4 g, 6.1 mmol) was added to a solution in which acetic acid of 20 mL and anhydride acetic acid of 40 mL were mixed, the solution was stirred at normal temperature for 10 minutes. The compound 1c (2.3 g, 6.1 mmol) obtained by the manufacture (2) was dissolved in acetic acid of 20 mL and then divided and slowly added to the above solution. After the resulting solution was further stirred for 2 hours, the reactant was poured into a beaker containing iced water, and generated solid sediments were filtered through a filter. A compound 1d of 2.4 g was obtained by washing and drying the reactant (Yield: 93%). Measurement results using $^1$H-NMR of the compound 1d are as follows.

1H NMR (500 MHz, CDCl$_3$, ppm): 9.06 (1H, s, ArH), 8.78 (1H, s, ArH), 8.43-8.41 (1H, d, ArH), 8.24-8.22 (1H, d, ArH), 7.51-7.49 (1H, d, ArH), 7.47-7.46 (1H, d, ArH), 4.41-4.38 (2H, t, CH$_2$), 3.38-3.36 (2H, t, CH$_2$), 2.75 (3H, s, COCH$_3$), 1.97-1.91 (2H, m, CH$_2$), 1.85-1.79 (2H, m, CH$_2$), 1.54-1.48 (2H, m, CH$_2$), 1.44-1.39 (2H, m, CH$_2$).

(4) Manufacture of 1e

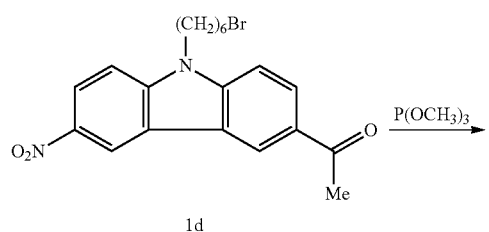

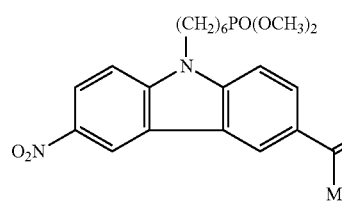

After the compound 1d (2.4 g, 5.7 mmol) obtained by the manufacture (3) was dissolved in trimethylphosphite of 20 mL in a temperature of 110° C., the compound was stirred under a nitrogen atmospheric current for 12 hours. The mixture was cooled at normal temperature, and remaining solvents were removed from the mixture under vacuum. Residues were dissolved in ethylacetate of 100 mL, and the residues pass through silica gels. Solvents were from the solution under vacuum, thereby obtaining a compound 1e of 2.0 g (Yield: 78%). Measurement results using $^1$H-NMR of the compound 1e are as follows.

1H NMR (500 MHz, CDCl$_3$, ppm): 9.07 (1H, s, ArH), 8.78 (1H, s, ArH), 8.44-8.42 (1H, d, ArH), 8.24-8.22 (1H, d, ArH), 7.50-7.49 (1H, d, ArH), 7.47-7.46 (1H, d, ArH), 4.40-4.37 (2H, t, CH$_2$), 3.72 (3H, s, OCH$_3$), 3.70 (3H, s, OCH$_3$), 2.75 (3H, s, COCH$_3$), 1.95-1.89 (2H, m, CH$_2$), 1.72-1.66 (2H, m, CH$_2$), 1.60-1.53 (2H, m, CH$_2$), 1.47-1.37 (4H, m, 2CH$_2$).

(5) Manufacture of 1f

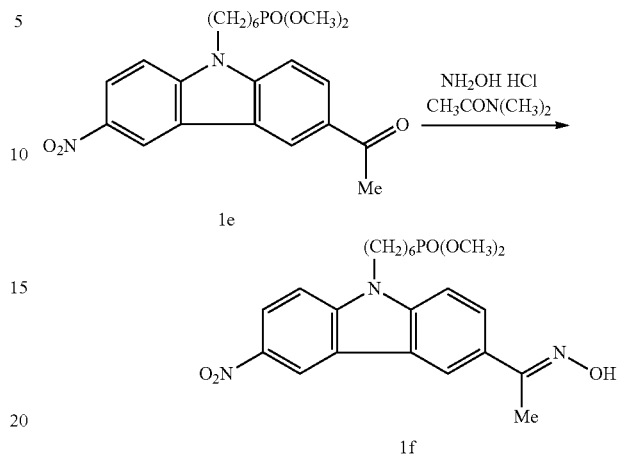

Hydroxyamine hydrochloride (0.4 g, 6.0 mmol) was added to a solution in which the compound 1e (1.8 g, 4.0 mmol) obtained by the manufacture (4) was dissolved in dimethylacetamide of 20 mL. The reactant was stirred in a temperature of 80° C. for 2 hours, cooled at normal temperature, and then poured into a beaker containing water. Generated solid sediments were filtered through a filter, and washing using water and dry were performed, thereby obtaining a compound 1f of 1.2 g (Yield: 66%). Measurement results using $^1$H-NMR of the compound 1f is as follows.

1H NMR (500 MHz, DMSO-D6, ppm): 11.09 (1H, s, NOH), 9.25 (1H, s, Ar), 8.67 (1H, s, Ar), 8.33-8.31 (1H, d, Ar), 7.97-7.95 (1H, d, Ar), 7.80-7.78 (1H, d, Ar), 7.72-7.70 (1H, d, Ar), 4.47-4.45 (2H, t, CH$_2$), 3.56 (3H, s, OCH$_3$), 3.54 (3H, s, OCH$_3$), 2.30 (3H, s, NOCH$_3$), 1.78-1.73 (2H, m, CH$_2$), 1.68-1.62 (2H, m, CH$_2$), 1.40-1.27 (6H, m, 3CH$_2$).

(6) Manufacture of a Photoactive Compound 1

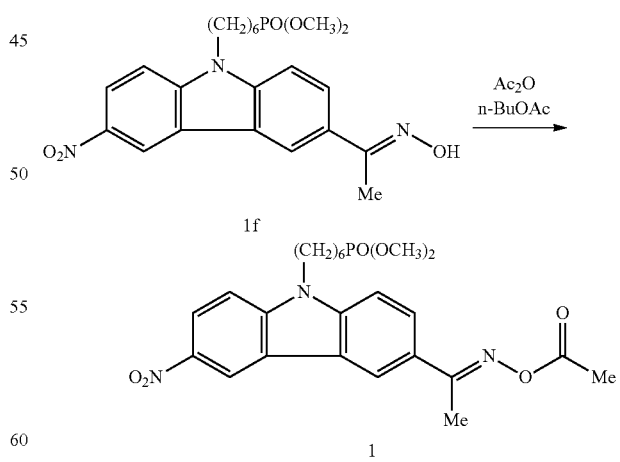

Anhydride acetic acid (0.4 g, 3.8 mmol) was added to a solution in which the compound 1f (1.2 g, 2.5 mmol) obtained by the manufacture (5) was dissolved in n-butylacetate of 30 mL. The reactant was stirred in a temperature of 90° C. for 2 hours and then cooled at normal temperature. Hexane of 20 mL was added to the reactant. Next, generated solid sediments were filtered through a filter, thereby obtaining the photoactive compound 1 of 1.0 g after dry (Yield: 83%). A measurement result using $^1$H-NMR of the photoactive compound 1 represented by Chemical Formula 1 is as follows.

1H NMR (500 MHz, CDCl$_3$, ppm): 9.05 (1H, s, Ar), 8.50 (1H, s, Ar), 8.42-8.40 (1H, d, Ar), 8.07-8.05 (1H, d, Ar), 7.47-7.46 (1H, d, Ar), 7.44-7.42 (1H, d, Ar), 4.38-4.35 (2H, t, CH$_2$), 3.72 (3H, s, OCH$_3$), 3.70 (3H, s, OCH$_3$), 2.54 (3H, s, NOCH$_3$), 2.31 (3H, s, COCH$_3$), 1.94-1.88 (2H, m, CH$_2$), 1.72-1.65 (2H, m, CH$_2$), 1.60-1.52 (2H, m, CH$_2$), 1.46-1.36 (4H, m, 2CH$_2$).

Embodiment 2: Manufacture of a Photoactive Compound 2

(1) Manufacture of 2a

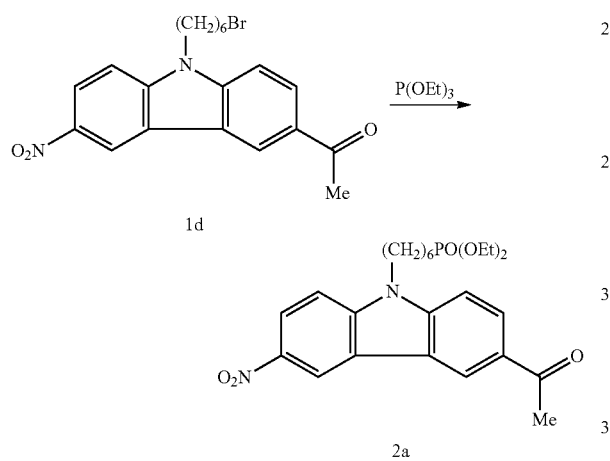

The compound 1d (1.9 g, 4.5 mmol) obtained by the manufacture (3) in Embodiment 1 was dissolved in triethylphosphite of 20 mL and then stirred in a temperature of 150° C. under a nitrogen atmospheric current for 3 hours. The mixture was cooled at normal temperature, and remaining solvents were removed from the mixture under vacuum, thereby obtaining a compound 2a of 2.0 g (Yield: 93%)

1H NMR (500 MHz, CDCl$_3$, ppm): 9.05 (1H, s, ArH), 8.75 (1H, s, ArH), 8.42 (1H, d, ArH), 8.20 (1H, d, ArH), 7.50-7.49 (1H, d, ArH), 7.47-7.46 (1H, d, ArH), 4.40-4.37 (2H, t, CH$_2$), 4.16-4.05 (4H, m, 2OCH$_2$), 3.70 (3H, s, OCH$_3$), 2.75 (3H, s, COCH$_3$), 1.95-1.89 (2H, m, CH$_2$), 1.72-1.66 (2H, m, CH$_2$), 1.60-1.53 (2H, m, CH$_2$), 1.47-1.37 (4H, m, 2CH$_2$), 1.35-1.24 (6H, m, 2CH$_3$).

(2) Manufacture of 2b

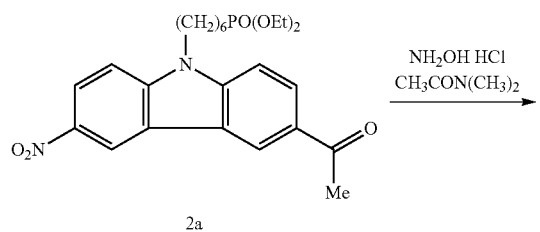

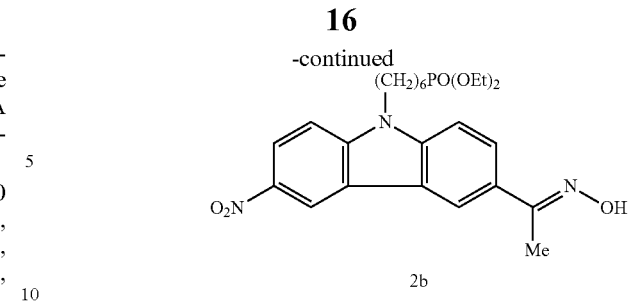

Hydroxyamine hydrochloride (0.4 g, 6.2 mmol) was added to a solution in which the compound 2a (2.0 g, 4.2 mmol) obtained by the manufacture (1) was dissolved in dimethylacetamide of 20 mL. The reactant was stirred in a temperature of 80° C. for 2 hours, cooled at normal temperature, and then poured into a beaker containing water. Next, generated solid sediments were filtered through a filter, and washing using water and dry were performed, thereby obtaining the photoactive compound 2b of 0.7 g (Yield: 35%).

1H NMR (500 MHz, acetone d6, ppm): 10.40 (1H, s, NOH), 9.18 (1H, s, Ar), 8.69 (1H, s, Ar), 8.39-8.37 (1H, d, Ar), 8.05-8.03 (1H, d, Ar), 7.81-7.79 (1H, d, Ar), 7.72-7.70 (1H, d, Ar), 4.58-4.55 (2H, t, CH$_2$), 4.03-3.99 (4H, q, 2 OCH$_2$CH$_3$), 2.40 (3H, s, NOCH$_3$), 1.96-1.93 (2H, m, CH$_2$), 1.69-1.63 (2H, m, CH$_2$), 1.56-1.45 (6H, m, 3CH$_2$), 1.25-1.22 (6H, t, 2 OCH$_2$H$_3$).

(3) Manufacture of a Photoactive Compound 2

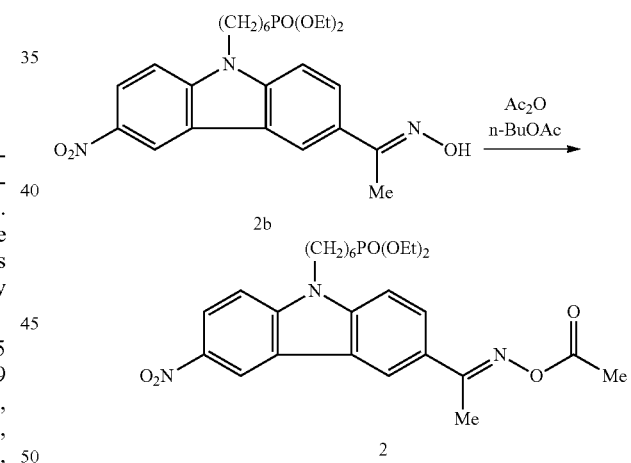

Anhydride acetic acid (0.2 g, 2.1 mmol) was added to a solution in which the compound 2b (0.7 g, 1.4 mmol) obtained by the manufacture (2) was dissolved in n-butylacetate of 30 mL. The reactant was stirred in a temperature of 90° C. for 2 hours and then cooled at normal temperature. Hexane of 60 mL was added to the reactant. Next, generated solid sediments were filtered through a filter, and dry was then performed, thereby obtaining the photoactive compound 2 of 0.5 g represented by the above chemical formula (Yield: 71%).

1H NMR (500 MHz, CDCl$_3$, ppm): 9.06 (1H, s, Ar), 8.51 (1H, s, Ar), 8.42-8.40 (1H, d, Ar), 8.07-8.05 (1H, d, Ar), 7.48-7.46 (1H, d, Ar), 7.45-7.43 (1H, d, Ar), 4.38-4.36 (2H, t, CH$_2$), 4.08-4.04 (4H, q, 2 OCH$_2$CH$_3$), 2.54 (3H, s, NOCH$_3$), 2.31 (3H, s, COCH$_3$), 1.94-1.88 (2H, m, CH$_2$), 1.70-1.64 (2H, m, CH$_2$), 1.61-1.52 (2H, m, CH$_2$), 1.46-1.36 (4H, m, 2CH$_2$), 1.31-1.28 (6H, t, 2 OCH$_2$CH$_3$).

Embodiment 3: Manufacture of a Photoactive Compound 3

(1) Manufacture of 9-(3-chloropropyl)-carbazole(9-(3-chloropropyl)-carbazole) 3b

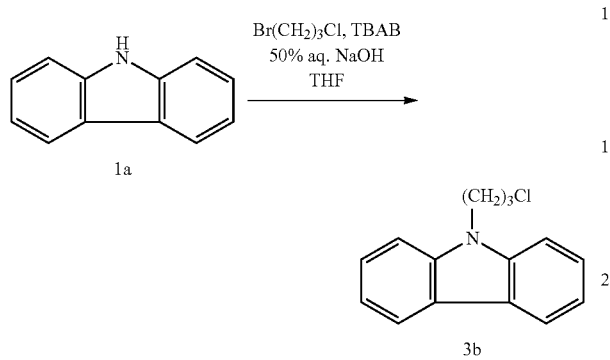

Tetrabutylammoniumbromide (1.3 g, 4.0 mmol), 1-bromo-3-chloropropane (47.2 g, 300 mmol), and a 50% aqueous sodium hydroxide solution of 300 mL were slowly added to a solution in which carbazole (33.4 g, 200 mmol) represented by Chemical Formula 1a was dissolved in tetrahydrofuran of 100 mL, under a nitrogen atmospheric current. The mixture was stirred in a temperature of 40° C. for 5 hours. An organic layer was separated from the mixture by adding ethylacetate of 100 g and water of 300 g to the mixture. Next, water was removed from the mixture using anhydrous magnesium sulfate, and solvents were removed from the mixture under vacuum, thereby obtaining the compound 3b of 47.8 g (Yield: 98%).

1H NMR (500 MHz, CDCl$_3$, ppm): 8.07 (2H, d, ArH), 7.44 (2H, t, ArH), 7.43 (2H, d, ArH), 7.22 (2H, t, ArH), 4.44 (2H, t, CH$_2$), 3.45 (2H, t, CH$_2$), 2.30-2.25 (2H, m, CH$_2$).

(2) Manufacture of 3c

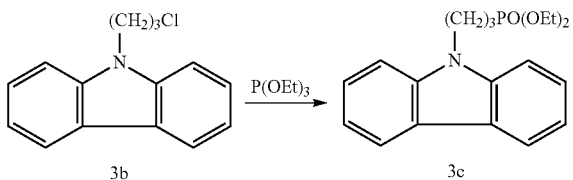

The compound 3b (12.2 g, 50 mmol) obtained by the manufacture (1) was dissolved in triethylphosphite (84 g, 500 mmol) in a temperature of 150° C. and was then stirred under a nitrogen atmospheric current for 18 hours. The mixture was cooled at normal temperature, and remaining solvents were removed from the mixture under vacuum. Residues were dissolved in ethylacetate of 100 mL, and the residues pass through silica gels. Next, solvents were removed from the residues under vacuum, thereby obtaining a compound of 10.1 g represented by Chemical Formula 3c (Yield: 58%).

1H NMR (500 MHz, CDCl$_3$, ppm): 8.09 (2H, d, ArH), 7.45 (2H, t, ArH), 7.44 (2H, d, ArH), 7.23 (2H, t, ArH), 4.42 (2H, t, CH$_2$), 4.18-4.02 (4H, m, 2OCH$_2$), 2.25-2.12 (2H, m, CH$_2$), 1.80-1.67 (2H, m, CH$_2$), 1.33-1.25 (6H, m, 2CH$_3$).

(3) Manufacture of 3d

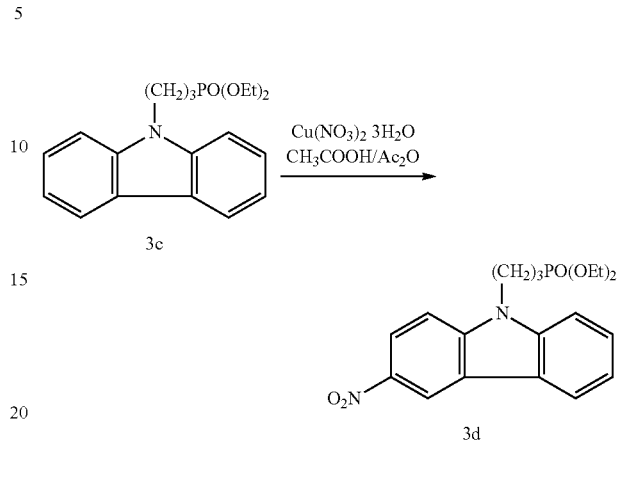

Copper nitrate hydrate (2.4 g, 10 mmol) was added to a solution in which acetic acid of 20 mL and anhydride acetic acid of 40 mL were mixed and was then stirred at normal temperature for 10 minutes. The compound 3c (9.2 g, 20 mmol) obtained by the manufacture (2) was dissolved in acetic acid of 20 mL, divided and slowly added to the above solution, and further stirred for 2 hours. The reactant was poured into a beaker containing iced water, and generated solid sediments were filtered through a filter. Next, the reactant was washed using water and dried, thereby obtaining a compound 3d of 5.0 g (Yield: 64%).

1H NMR (500 MHz, CDCl$_3$, ppm): 9.00 (1H, s, ArH), 8.39 (1H, d, ArH), 8.14 (1H, d, ArH), 7.59-7.46 (3H, m, ArH), 7.37-7.26 (1H, m, ArH), 4.50 (2H, t, CH$_2$), 4.16-4.04 (4H, m, 2OCH$_2$), 2.27-2.15 (2H, m, CH$_2$), 1.85-1.64 (2H, m, CH$_2$), 1.35-1.25 (6H, m, 2CH$_3$).

(4) Manufacture of 3e

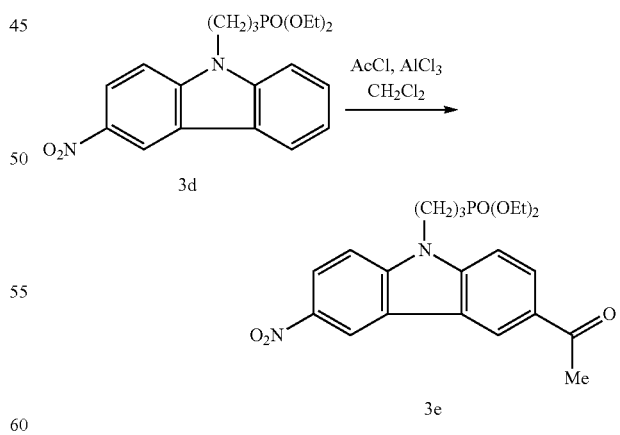

The compound 3d (5.0 g, 12.8 mmol), obtained by the manufacture (3), and acetyl chloride (1.4 mL, 19.2 mmol) were dissolved in dichloromethane of 50 mL. Next, aluminum chloride (2.6 g, 19.2 mmol) was divided and slowly added to the solution in a temperature range of 0 to 10° C. and then stirred in the temperature range of 0 to 10° C. for 2 hours.

The solution was further stirred at normal temperature for 5 hours. After the reactant was poured into a beaker containing iced water, an organic layer was extracted from the reactant. After the solution was washed using a saturated NaHCO3 aqueous solution, water was removed from the solution using anhydrous magnesium sulfate. Solvents were removed from the solution under vacuum, and the solution was refined using column(ethylacetate:methanol=10:1), thereby obtaining acylating 3e of 3.5 g (Yield: 63%).

1H NMR (500 MHz, CDCl$_3$, ppm): 8.92 (1H, s, ArH), 8.69 (1H, s, ArH), 8.34 (1H, d, ArH), 8.19 (1H, d, ArH), 7.57-7.46 (2H, d, ArH), 4.52 (2H, t, CH$_2$), 4.16-4.05 (4H, m, 2OCH$_2$), 2.73 (3H, s, CH$_3$), 2.30-2.16 (2H, m, CH$_2$), 1.85-1.64 (2H, m, CH$_2$), 1.35-1.24 (6H, m, 2CH$_3$).

(5) Manufacture of 3

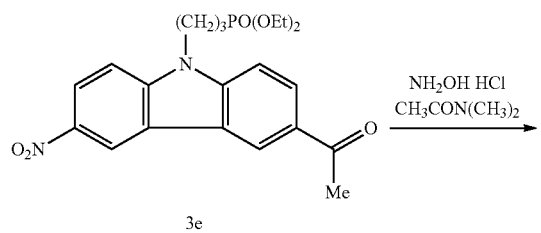

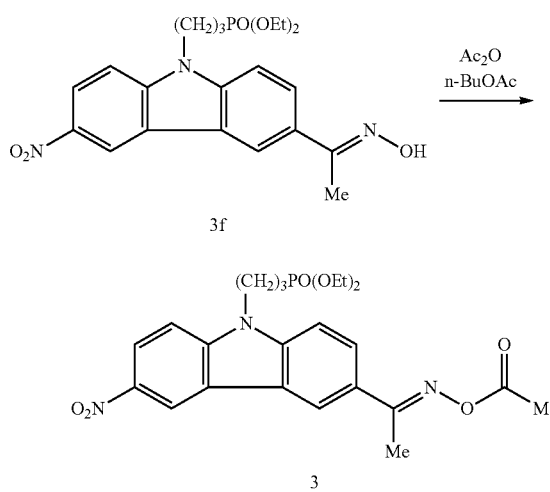

Hydroxyamine hydrochloride (0.4 g, 6.2 mmol) was added to a solution in which the compound 3e (1.8 g, 4.2 mmol) obtained by the manufacture (4) was dissolved in dimethylacetamide of 20 mL. The reactant was stirred in a temperature of 80° C. for 2 hours, cooled at normal temperature, and then poured into a beaker containing water. Ethylacetate of 20 mL was added to the reactant, and an organic layer was removed from the reactant. Next, a compound 3f was obtained by removing water from the reactant using anhydrous magnesium sulfate and by removing solvents from the reactant under vacuum. Anhydride acetic acid (0.6 mL, 6.4 mmol) was added to a solution in which the compound 3f was dissolved in n-butylacetate of 20 mL. The reactant was stirred in a temperature range of 90° C. for 2 hours, cooled at normal temperature, and then poured in a beaker containing water. The photoactive compound 3 of 1.4 g was obtained by extracting an organic layer, removing water using anhydrous magnesium sulfate, removing solvents under vacuum, and then refining the reactant using column (ethylacetate:methanol=10:1) (Yield: 77%).

1H NMR (500 MHz, CDCl$_3$, ppm): 8.75 (1H, s, ArH), 8.33 (1H, s, ArH), 8.24 (1H, d, ArH), 7.94 (1H, d, ArH), 7.47-7.43 (2H, d, ArH) 4.43 (2H, t, CH$_2$), 4.16-4.05 (4H, m, 2OCH$_2$), 2.50 (3H, s, CH$_3$), 2.34 (3H, s, CH$_3$), 2.26-2.16 (2H, m, CH$_2$), 1.89-1.67 (2H, m, CH$_2$), 1.36-1.24 (6H, m, 2CH$_3$).

Embodiment 4: Manufacture of a Photoactive Compound 4

(1) Manufacture of 4a

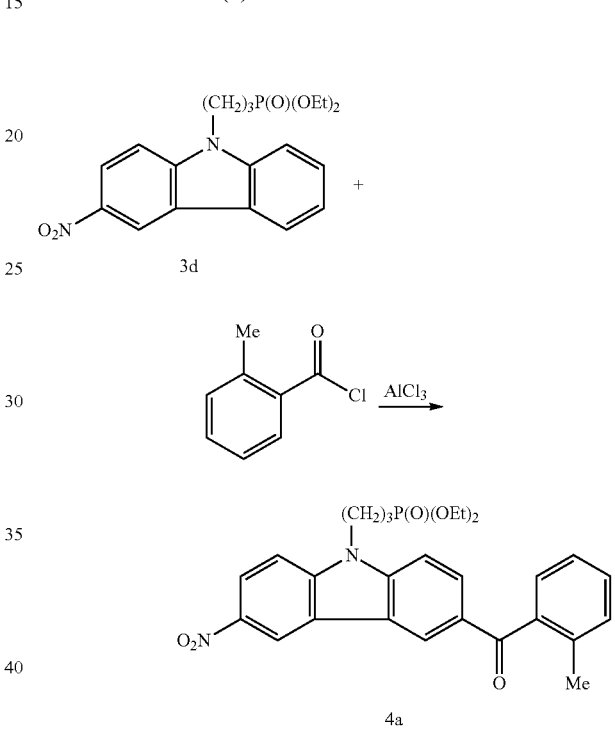

The compound 3d (2.5 g, 6.4 mmol), obtained by the manufacture (3) in Embodiment 3, and toluoyl chloride (1.3 mL, 9.6 mmol) were dissolved in dichloromethane of 12 mL. Aluminum chloride (2.1 g, 12.8 mmol) was divided and slowly added to the above solution in a temperature range of 0 to 10° C. and was then stirred at normal temperature for 1 hour. After the reactant was poured into a beaker containing iced water, an organic layer was extracted from the reactant. The reactant was washed using a saturated NaHCO$_3$ aqueous solution. Acylating 4a of 1.7 g was obtained by removing water using anhydrous magnesium sulfate, removing solvents under vacuum, and then refining the reactant using column (ethylacetate) (Yield: 52%). A measurement result using $^1$H-NMR of the acylating is as follows.

1H NMR (500 MHz, CDCl$_3$, ppm): 8.97 (1H, d, ArH), 8.52 (1H, dd, ArH), 8.43 (1H, dd, ArH), 8.19 (1H, dd, ArH), 7.61-7.58 (2H, m, ArH), 7.48-7.45 (1H, ddd, ArH), 7.39-7.36 (2H, m, ArH), 7.34-7.31 (1H, m, ArH), 4.57 (2H, t, NCH$_2$), 4.17-4.06 (4H, m, 2OCH$_2$), 2.36 (3H, s, CH$_3$), 2.29-2.19 (2H, m, CH$_2$), 1.79 (2H, dt, PCH$_2$), 1.32 (6H, t, 2CH$_3$)

(2) Manufacture of 4b

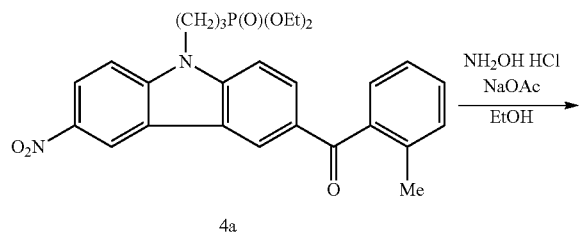

4a

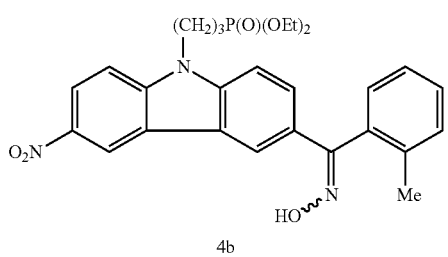

4b

Hydroxyamine hydrochloride (1.4 g, 19.8 mmol) and sodiumacetate (1.1 g, 13.2 mmol) were added to a solution in which the compound 4a (3.4 g, 6.6 mmol) obtained by the manufacture (1) was dissolved in ethanol of 15 mL. The reactant was re-fluxed for 60 hours, cooled at normal temperature, diluted using ethylacetate. The resulting solid deposit was filtered using a filter and then dried. The solid deposit was diluted using ethylacetate and then washed using a saturated NaHCO$_3$ aqueous solution. A compound 4b of 3.4 g was obtained by removing water using anhydrous magnesium sulfate and removing solvents under vacuum (Yield: 99%). A measurement result using $^1$H-NMR of the compound 4b is as follows.

1H NMR (500 MHz, CDCl$_3$, ppm): 8.88 (1H, d, ArH), 8.36 (1H, dd, ArH), 8.06 (1H, dd, ArH), 7.87 (1H, dd, ArH), 7.51-7.47 (2H, m, ArH), 7.45-7.34 (3H, m, ArH), 7.20 (1H, dd, ArH), 4.50 (2H, t, NCH$_2$), 4.16-4.05 (4H, m, 2OCH$_2$), 2.25 (3H, s, CH$_3$), 2.27-2.17 (2H, m, CH$_2$), 1.77 (2H, dt, PCH$_2$), 1.31 (6H, t, 2CH$_3$)

(3) Manufacture of a Photoactive Compound 4

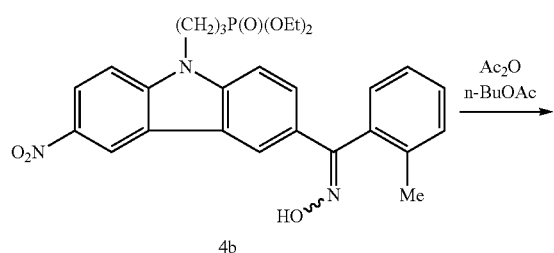

4b

-continued

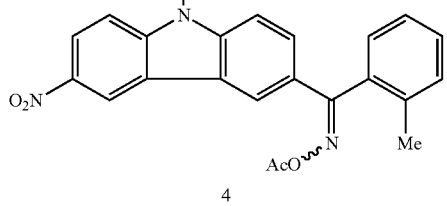

4

Anhydride acetic acid (1.0 g, 9.7 mmol) was added to a solution in which the compound 4b (3.4 g, 6.5 mmol) obtained by the manufacture (2) was dissolved in n-butylacetate of 15 mL. The reactant was stirred in a temperature of 90° C. for 2 hours, cooled at normal temperature, diluted using saturated ethylacetate, and then washed using a NaHCO$_3$ aqueous solution. The photoactive compound 4 of 3.4 g was obtained by removing water using anhydrous magnesium sulfate, removing solvents under vacuum, and refining the reactant using column (ethylacetate) (Yield: 52%). A measurement result using $^1$H-NMR of the photoactive compound 4 represented by Chemical Formula 4 above is as follows.

1H NMR (500 MHz, CDCl$_3$, ppm): 8.91 (1H, d, ArH), 8.39 (1H, dd, ArH), 8.16 (1H, dd, ArH), 8.05 (1H, dd, ArH), 7.53 (2H, dd, ArH), 7.45 (1H, ddd, ArH), 7.39-7.33 (2H, m, ArH), 7.16 (1H, d ArH), 4.52 (2H, t, NCH$_2$), 4.16-4.05 (4H, m, 2OCH$_2$), 2.20 (3H, s, CH$_3$), 2.21-2.18 (2H, m, CH$_2$), 2.07 (3H, s, COCH$_3$), 1.77 (2H, dt, PCH$_2$), 1.31 (6H, t, 2CH$_3$)

Embodiment 5: Manufacture of a Transparent Resin Composition

A photosensitive composition solution was obtained by mixing alkali-soluble binder resin of 12 g (that is, a copolymer of benzylmethacrylate/methacrylicacid (BzMA/MAA) (mole ratio: 70/30, Mw: 10,000, acid value 115 KOH mg/g), dipentaerythritol hexaacrylate of 17 g (that is, a polymerizable compound having an ethylene-based unsaturated bond, KBM-503 of 0.5 g (that is, an adhesive aid), BYK-307 of 0.05 g (that is, a surfactant), the photoactive compound (1) of 2.5 g fabricated in Embodiment 1 and listed in Table 1 below, and PGMEA of 67.95 g (that is, an organic solvent) using shaker for 3 hours.

Embodiment 6: Manufacture of a Transparent Photosensitive Resin Composition

A photosensitive resin composition was fabricated using the same method as that used in Embodiment 5 except that the compound (2) of 2.5 g, obtained in Embodiment 2, was used as a photoactive compound instead of the photoactive compound (1) listed in Table 1 below.

Embodiment 7: Manufacture of a Transparent Photosensitive Resin Composition

A photosensitive resin composition was fabricated using the same method as that used in Embodiment 5 except that the compound (3) of 2.5 g, obtained in Embodiment 3, was used as a photoactive compound instead of the photoactive compound (1) listed in Table 1 below.

Embodiment 8: Manufacture of a Transparent Photosensitive Resin Composition

A photosensitive resin composition was fabricated using the same method as that used in Embodiment 5 except that the compound (4) of 2.5 g, obtained in Embodiment 4, was used as a photoactive compound instead of the photoactive compound (1) listed in Table 1 below.
TABLE 1
| Photoactive Compound | |
|---|---|
| Compound 1 | 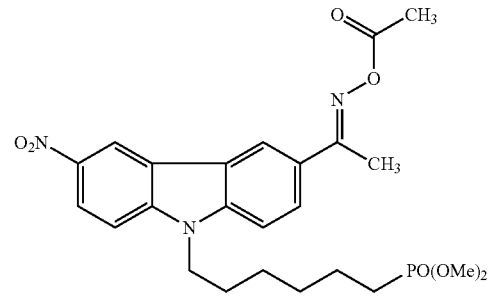 |
| Compound 2 | 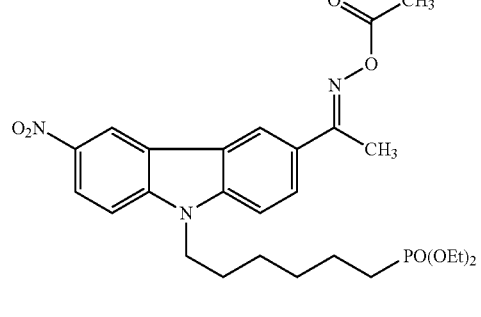 |
| Compound 3 | 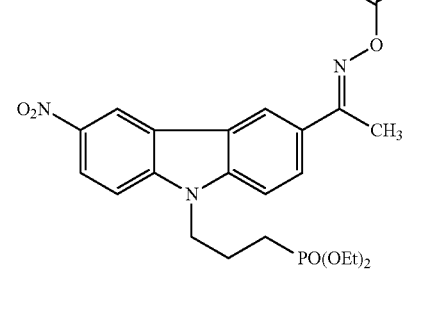 |
| Compound 4 | 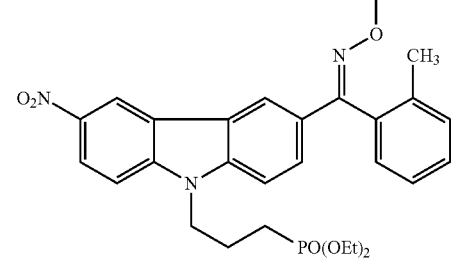 |
TABLE 1-continued
| Photoactive Compound | |
|---|---|
| Compound 5 | |
| Compound 6 | Irgacure OXE-02 |
| Compound 7 | |
| Compound 8 | |
| Compound 9 | |

COMPARISON EXAMPLE 1

A photosensitive resin composition was fabricated using the same method as that used in Embodiment 5 except that a compound (5) of 2.5 g in Table 1 was used as a photoactive compound instead of the photoactive compound (1) listed in Table 1.

COMPARISON EXAMPLE 2

A photosensitive resin composition was fabricated using the same method as that used in Embodiment 5 except that Irgacure OXE-02 (compound 6) of 2.5 g in Table 1 was used as a photoactive compound instead of the photoactive compound (1) listed in Table 1.

COMPARISON EXAMPLE 3

A photosensitive resin composition was fabricated using the same method as that used in Embodiment 5 except that a compound (7) of 2.5 g in Table 1 was used as a photoactive compound instead of the photoactive compound (1) listed in Table 1.

COMPARISON EXAMPLE 4

A photosensitive resin composition was fabricated using the same method as that used in Embodiment 5 except that a compound (8) of 2.5 g in Table 1 was used as a photoactive compound instead of the photoactive compound (1) listed in Table 1.

COMPARISON EXAMPLE 5

A photosensitive resin composition was fabricated using the same method as that used in Embodiment 5 except that a compound (9) of 2.5 g in Table 1 was used as a photoactive compound instead of the photoactive compound (1) listed in Table 1.

Evaluation 1 of Physical Properties

Maximum UV absorption wavelengths in the compounds 1 to 8 listed in Table 1 were measured, and results of the measurement are listed in Table 2 below.

TABLE 2

| Photoactive Compound | $\lambda$max (nm) |
| --- | --- |
| Compound 1 | 372 |
| Compound 2 | 372 |
| Compound 3 | 372 |
| Compound 4 | 372 |
| Compound 5 | 318 |
| Compound 6 | 338 |
| Compound 7 | 372 |
| Compound 8 | 371 |
| Compound 9 | 370 |

From Table 2, it can be seen that the photoactive compounds (compound 1 to 4) according to the present invention have the maximum UV absorption wavelength of 372 nm and better light absorption efficiency because they have the maximum UV absorption wavelength of 372 nm close to the i-line (365 nm) of an exposure system, as compared with the conventional photoinitiators (compounds 5 and 6) including other oxime ester groups. Furthermore, the compounds 7 to 9 have similar maximum UV absorption wavelengths to the photoactive compounds according to the present invention because they include nitro groups.

Evaluation 2 of Physical Properties

The transparent photosensitive compositions, fabricated in Embodiments 5 to 8 and Comparison Examples, were spin-coated on glass and then pre-baking processing in a temperature of about 95° C. for 70 seconds, thereby obtaining respective equal films each having a thickness of about 2.5 µm.

The films were exposed to light of 40 mJ/cm$^2$ and 100 mJ/cm$^2$ under a high pressure mercury lamp using a photomask for a circular isolated pattern of 20 µm in diameter, developed using a KOH alkali aqueous solution of pH 11.3 to 11.9, and then washed using deionized water. The films were subjected to post-baking processing in a temperature of 210° C. for about 20 minutes. Physical properties of patterns of the films were measured using the following method, and results of the measurement are listed in Table 4 below.

1) Lower Critical-Dimension (CD)

The sizes of the patterns fabricated by exposing the patterns to the same amount of light of 40 mJ/cm$^2$ in the embodiments and the comparison examples were measured using a pattern profiler, and diameters of portions corresponding to lower 10% were indicated by a low CD. Since the exposure was performed using the same amount of light, compositions using an initiator having better photoinitiation efficiency were better crosslinked upon exposure, thus having greater patterns. Accordingly, it can be said that sensitivity is better with an increase in the CD value.

2) Upper CD

The sizes of the patterns fabricated by exposing the patterns to the same amount of light of 40 mJ/cm$^2$ in the embodiments and the comparison examples were measured using a pattern profiler, and diameters of portions corresponding to lower 5% were indicated by an upper CD. Since the exposure was performed using the same amount of light, compositions using an initiator having better photoinitiation efficiency were better crosslinked upon exposure, thus having greater patterns. Accordingly, it can be said that sensitivity is better with an increase in the CD value.

3) Pattern Thickness and Step

The thickness of patterns generated using a low amount of exposure light (40 mJ/cm$^2$) and of patterns generated using a high amount of exposure light (100 mJ/cm$^2$), in the embodiments and the comparison examples, was measured, and a difference in the thickness was calculated. Results of the measurement are listed in Table 3 below. With a decrease in the step value, it means that patterns are stably formed even by a small amount of light energy. The patterns can be said to have an excellent characteristic.

TABLE 3

| | Photoactive compound | Exposure 40 mJ | | | Exposure 100 mJ Pattern thickness(μm) | Step (nm) |
|---|---|---|---|---|---|---|
| | | Lower CD (μm) | Upper CD (μm) | Pattern thickness(μm) | | |
| Embodiment 5 | Compound 1 | 45.0 | 27.4 | 2.574 | 2.584 | 10.0 |
| Embodiment 6 | Compound 2 | 44.3 | 27.2 | 2.593 | 2.604 | 10.3 |
| Embodiment 7 | Compound 3 | 45.9 | 27.3 | 2.561 | 2.567 | 6.7 |
| Embodiment 8 | Compound 4 | 47.8 | 27.0 | 2.535 | 2.542 | 7.0 |
| Co. Ex. 1 | Compound 5 | Pattern fallen off | | | 1.427 | — |
| Co. Ex. 2 | Compound 6 | 41.0 | 24.2 | 2.437 | 2.499 | 62.7 |
| Co. Ex. 3 | Compound 7 | Photoinitiator not used | | | | |
| Co. Ex. 4 | Compound 8 | Photoinitiator not used | | | | |
| Co. Ex. 5 | Compound 9 | Photoinitiator not used | | | | |

※Co. Ex. indicates an abbreviation of Comparison Example.

As shown in Table 3, if the photoactive compound, comprising the nitro group and the phosphonate structure, according to the present invention is used as the photopolymerization initiator of a photosensitive resin composition, a sufficient amount of the photoactive compound can be used because compatibility for a photosensitizer is good. Accordingly, a sensitivity characteristic preferably can be improved.

The above results show that the patterns fabricated according to Embodiments 5 to 8 have a high sensitivity characteristic in which the patterns have greater upper and lower CDs and a less difference in the thickness according to a shift of the amount of light exposure, than the patterns fabricated according to Comparison Examples 1 and 2. The photosensitive composition fabricated according to Comparison Example 1 did not form a pattern in a low amount of light exposure of 40 mJ because of its low sensitivity. Comparison Examples 3 to 5 exhibited a problem that a sufficient amount was not used in order to obtain desired sensitivity because the photoactive compounds 7 to 9 of Comparison Examples 3 to 5 did not melt because of their poor solubility for a photosensitive composition, but formed deposition.

If the photoactive compound comprising the phosphonate structure is used as a photopolymerization initiator in the transparent photosensitive composition of the present invention, the phosphonate group and the alkali-soluble binder resin, included in the photoactive compound, form hydrogen bonds, thereby increasing compatibility between the photoactive compound and the binder resin and thus increasing solubility within the photosensitive composition. Accordingly, the photoactive compound of the present invention can be preferably used in sufficient quantities in order to obtain high sensitivity.

The photosensitive resin composition comprising the photoactive compound according to the present invention exhibits excellent sensitivity through efficient absorption for UV light, excellent compatibility between the photoactive compound and the alkali-soluble binder resin, and an improved solubility of the photosensitive resin composition. Furthermore, the photosensitive resin composition of the present invention has excellent residual film thickness and mechanical strength characteristics and heat-resistant, chemical-resistant, and development-resistant properties. Accordingly, the photosensitive resin composition of the present invention is advantageous in hardening the column spacers of liquid crystal displays, an overcoat, and passivation materials and also advantageous in a high-temperature process characteristic.

What is claimed is:
1. A photoactive compound represented by Chemical Formula 1 below:

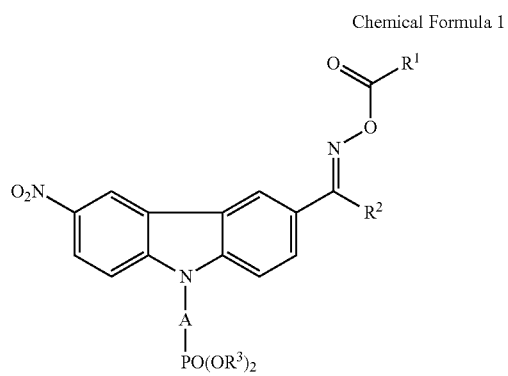

Chemical Formula 1 wherein, each of R1 and R2 independently is hydrogen, halogen, cyano, —R, —OR, —SR, —COR, —OCOR, —NRR', or —CONRR' group,
R3 is an alkyl group of C1 to C8 or an aryl group of C6 to C12, and
A is an alkylene group of C2 to C15 unsubstituted or substituted with one or more substituents selected from the group consisting of —R, —OR, —SR, —COR, and —OCOR groups, and
each of the R and R' is an alkyl group of C1 to C10, a halo alkyl group of C1 to C10, or an aralkyl group of C7 to C13, or R and R' taken together form a ring.

2. A photosensitive resin composition, comprising:
a photoactive compound represented by Chemical Formula 1 below:
an alkali-soluble binder resin;
a polymerizable compound having an ethylene-based unsaturated bond; and
a solvent, Chemical Formula 1

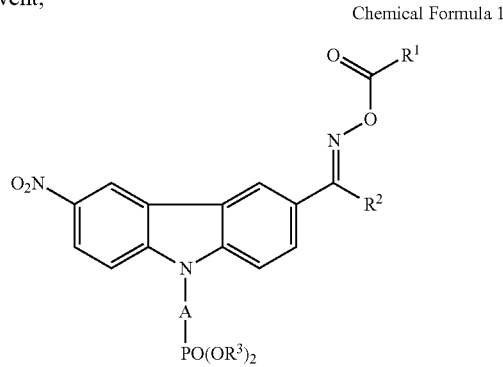

wherein, each of R1 and R2 independently is hydrogen, halogen, cyano, —R, —OR, —SR, —COR, —OCOR, —NRR', or —CONRR' group, R3 is an alkyl group of C1 to C8 or an aryl group of C6 to C12, and A is an alkylene group of C2 to C15 unsubstituted or substituted with one or more substituents selected from the group consisting of —R, —OR, —SR, —COR, and —OCOR groups, and each of the R and R' is an alkyl group of C1 to C10, a halo alkyl group of C1 to C10, or an aralkyl group of C7 to C13, or R and R' taken together form a ring.

3. The photosensitive resin composition of claim 2, wherein the alkali-soluble binder resin has an acid value of 30 to 300 KOH mg/g.

4. The photosensitive resin composition of claim 2, wherein the alkali-soluble binder resin has a weight average molecular weight of 1,000 to 200,000.

5. The photosensitive resin composition of claim 2, wherein the polymerizable compound having an ethylene-based unsaturated bond comprises one or more kinds selected from a group consisting of:
a compound obtained by esterifying polyhydric alcohol using α, β-unsaturated carboxylic acid;
a compound obtained by adding (meth)acrylic acid to a compound containing a glycidyl group;
an adduct of a compound having an OH group or an ethylene-based unsaturated bond and an ester compound with polyhydric carboxylic acid or polyisocyanate; and (meth)acrylic acid alkylester; and
9,9'-bis[4-(2-acryloyloxyethoxy)phenyl]fluorene.

6. The photosensitive resin composition of claim 2, wherein the photosensitive resin composition comprises 0.1 to 5 wt % of the photoactive compound represented by Chemical Formula 1, 1 to 20 wt % of the alkali-soluble binder resin, 0.5 to 20 wt % of the polymerizable compound having an ethylene-based unsaturated bond, and 10 to 95 wt % of the solvent based on the total weight of the photosensitive resin composition.

7. The photosensitive resin composition of claim 2, wherein the photosensitive resin composition further comprises a second photoactive compound comprising one or more kinds selected from a group consisting of a triazine-based compound, a non-imidazole-based compound, an acetophenone-based compound, an O-acyloxime-based compound, a benzophenone-based compound, a thioxanthone-based compound, a phosphine oxide-based compound, and a courmarin-based compound.

8. The photosensitive resin composition of claim 7, wherein the second photoactive compound is contained in an amount of 0.1 to 5 wt % based on the total weight of the photosensitive resin composition.

9. The photosensitive resin composition of claim 5, wherein the compound obtained by esterifying polyhydric alcohol using α,β-unsaturated carboxylic acid is at least one selected from the group consisting of dipentaerythritol hexa (meth)acrylate, an acid variant of ethyleneglycol di(meth)acrylate and polyethylene glycol di(meth)acrylate in which the number of ethylene groups is 2 to 14, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic, propylene glycol di(meth)acrylate in which the number of propylene groups is 2 to 14, dipentaerythritol pentameth)acrylate, dipentaerythritol pentameth)acrylate, and dipentaerythritol hexa(meth)acrylate.

10. The photosensitive resin composition of claim 5, wherein the compound having an ethylene-based unsaturated bond compound is one or more kinds selected from the group consisting of phthlatediester of β-hydroxyethyl(meth)acrylate, a toluene diisocyanate adduct of β-hydroxyethyl (meth) acrylate, allyl glycidyl ether, glycidyl (meth)acrylate, 3,4-epoxycyclohexylmethyl (meth)acrylate, glycidyl 5-norbornene-2- methyl-2-carboxylate(endo, exo mixture), 1,2-epoxy-5-hexene, and 1,2-epoxy-9- decene.

11. The photosensitive resin composition of claim 2, wherein the alkali-soluble resin binder is a polymer of a monomer comprising an acid functional group, a copolymer with a monomer copolymerizable with a monomer having an acid functional group, or an ethylene-based unsaturated compound comprising the copolymer and an epoxy group.

* * * * *